United States Patent
Pumarola Segura et al.

(10) Patent No.: US 10,233,206 B2
(45) Date of Patent: Mar. 19, 2019

(54) D-FAGOMINE FOR THE CONTROL OF INFLAMMATORY PROCESSES RELATED TO AN OVERACTIVATION OF THE HUMORAL IMMUNE RESPONSE

(71) Applicants: Sergio Pumarola Segura, Barcelona (ES); BIOGLANE, S.L.N.E., Barcelona (ES)

(72) Inventors: Sergio Pumarola Segura, Barcelona (ES); Maria Carmen Antolin Mate, Sant Cugat del Valles (ES); Marta Llopis Pages, Barcelona (ES); Maria de los Angeles Calvo Torras, Barcelona (ES)

(73) Assignee: SERGIO PUMAROLA SEGURA (ES)

( * ) Notice: Subject to any disclaimer, the term of this patent is extended or adjusted under 35 U.S.C. 154(b) by 0 days.

(21) Appl. No.: 14/766,310

(22) PCT Filed: Feb. 13, 2014

(86) PCT No.: PCT/EP2014/052802
§ 371 (c)(1),
(2) Date: Aug. 6, 2015

(87) PCT Pub. No.: WO2014/125013
PCT Pub. Date: Aug. 21, 2014

(65) Prior Publication Data
US 2015/0368283 A1 Dec. 24, 2015

(30) Foreign Application Priority Data
Feb. 18, 2013 (EP) .................................. 13155586

(51) Int. Cl.
*A61K 31/445* (2006.01)
*A61K 36/00* (2006.01)
(Continued)

(52) U.S. Cl.
CPC .............. *C07H 5/06* (2013.01); *A23L 33/105* (2016.08); *A61K 31/445* (2013.01);
(Continued)

(58) Field of Classification Search
CPC ...... A61K 31/445; A61K 36/70; A23L 1/3002
(Continued)

(56) References Cited

U.S. PATENT DOCUMENTS 9,226,517 B2 * 1/2016 Pumarola Segura ........................ A23C 9/1322
2011/0171328 A1 * 7/2011 Zhou .................... A61K 31/445 424/729

FOREIGN PATENT DOCUMENTS

CN 1663448 9/2005
CN 101810276 8/2010
(Continued)

OTHER PUBLICATIONS

Kim et al. "Optimal Recovery of high-purity rutin crystals from the whole plant Fagopyrum esculentum Moench (Buckwheat) by extraction, fraction, and recrystallization." Bioresource Technology, 2005, vol. 96, pp. 1709-1712.*
(Continued)

*Primary Examiner* — Shengjun Wang
(74) *Attorney, Agent, or Firm* — Daniel A. Blasiole; Christopher M. Scherer; DeWitt LLP

(57) ABSTRACT

The present invention belongs to the field of nutraceuticals or functional agents with immunostimulating capacity for triggering mechanisms of the innate immune response at a mucosal level. More specifically, it refers to the use of the compound D-fagomine as immunostimulating agent of the innate immune response in the mucosa and for the prevention or prophylaxis of inflammatory processes or diseases associated with an overactivation of the humoral immune
(Continued)

response. The invention also relates to a composition comprising D-fagomine for the above referenced application.

18 Claims, 2 Drawing Sheets

(51) Int. Cl.
    *C07H 5/06*     (2006.01)
    *A61K 36/77*     (2006.01)
    *A61K 36/815*     (2006.01)
    *A61K 31/7048*     (2006.01)
    *A61K 36/48*     (2006.01)
    *A61K 36/605*     (2006.01)
    *A61K 36/70*     (2006.01)
    *A61K 31/7008*     (2006.01)
    *A23L 33/105*     (2016.01)

(52) U.S. Cl.
    CPC ...... *A61K 31/7008* (2013.01); *A61K 31/7048* (2013.01); *A61K 36/48* (2013.01); *A61K 36/605* (2013.01); *A61K 36/70* (2013.01); *A61K 36/77* (2013.01); *A61K 36/815* (2013.01)

(58) Field of Classification Search
    USPC .......................................... 424/776; 514/328
    See application file for complete search history.

(56) References Cited

FOREIGN PATENT DOCUMENTS

| | | |
|---|---|---|
| EP | 2255822 | 12/2010 |
| JP | 2006223285 A * | 8/2006 |
| WO | 2010029313 | 3/2010 |
| WO | 2011117362 | 9/2011 |
| WO | WO 2011/117362 A1 * | 9/2011 |
| WO | 2012007577 | 1/2012 |

OTHER PUBLICATIONS

Amezqueta et al. "The presence of D-fagomine in the human diet from buckwheat-based foodstuffs," Food Chemistry, 2013, vol. 136, pp. 1316-1321. Available online Sep. 18, 2012.*

Castillo et al., "Fructose-6-phosphate Aldolase in Organic Synthesis: Preparation of D-Fagomine, N-Alkylated Derivatives, and Preliminary Biological Assays," Organic Letters, 2006, 8(26):6067-6070.

Gomez et al., "D-Fagomine lowers postprandial blood glucose and modulates bacterial adhesion," British Journal of Nutrition, 2012, 107:1739-1746.

Kim et al., "Metabolic and Pharmacological Properties of Rutin, a Dietary Quercetin Glycoside, for Treatment of Inflammatory Bowel Disease," Pharmaceutical Research, Sep. 2005, 22(9):1499.

Torres et al., "D-Fagomine, an iminosugar with physiological effects on postprandial blood glucose and bacterial adhesion," 11th European Nutrition Conference, Ann Nutr Metab 2011, 58(Suppl 3):1.

Database Medline, Accession No. NLM22438663, U.S. National Library of Medicine, Jan. 2012, "Validated reversed phase-high performance liquid chromatography-diode array detector method for the quantitation of Rutin, a natural immunostimulant for improving survival in aquaculture practice, in toonea sinensis folium."

International Search Report and Written Opinion for PCT/EP2014/052802 dated Jun. 12, 2014.

* cited by examiner

D-FAGOMINE FOR THE CONTROL OF INFLAMMATORY PROCESSES RELATED TO AN OVERACTIVATION OF THE HUMORAL IMMUNE RESPONSE

CROSS REFERENCE TO RELATED APPLICATIONS

The present application is the U.S. national stage application of International Application PCT/EP2014/052802, filed Feb. 13, 2014, which international application was published on Aug. 21, 2014, as International Publication WO2014/125013. The International Application claims priority of European Patent Application 13155586.4, filed Feb. 18, 2013, the contents of which are incorporated herein by reference in their entireties.

FIELD OF THE INVENTION

The present invention belongs to the field of nutraceuticals or functional agents with immunostimulating capacity for triggering mechanisms of the immune response at a mucosal level. More specifically, it refers to the use of the compound D-fagomine as immunostimulating agent of the innate immune response in the mucosa and for the prevention or prophylaxis of clinical inflammatory processes, subclinical chronical inflammatory processes or diseases associated with opportunistic pathogens. The invention also relates to a composition comprising D-fagomine for the above referenced use.

BACKGROUND OF THE INVENTION

Nutraceuticals are products derived or isolated from natural or food sources that provide a benefit in the health of individuals consuming them or that prevent or delay the onset of certain disorders or diseases, in addition to the basic nutritional value thereof. That is the reason why the consumers are increasingly demanding this kind of products and why research and development in the field of nutraceuticals is becoming more and more important in the food, pharmaceutical and veterinary industry.

The research in the field of nutraceutical and functional foods is directed into different lines such as the identification and development of microorganisms that may confer a healthy benefit on the host, commonly known as probiotics, or the isolation of natural compounds or substances present in natural or food products which exert a beneficial effect on the health of the person consuming them.

One of the natural compounds that have proven to have beneficial effects in the health is D-fagomine.

D-fagomine (2R, 3R, 4R)-2-hydroxymethylpiperidine-3,4-diol, is a natural iminocyclitol, a polyhydroxylated piperidine which was first isolated from buckwheat seeds of *Faqopyrum esculentum* Moench and later from other plant sources such as mulberry (*Morus alba*, Moraceae), gogi (*Lyceum chinense*), *Castanospermum australe*, *Xhanthocercis zambesiaca* leaves and *Morus bombycis* leaves. The D-fagomine (2R, 3R, 4R)-2-hydroxymethylpiperidine-3,4-diol is shows in the formula below.

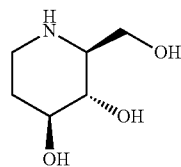

Among other functions, D-fagomine has been taught to decrease postprandrial blood glucose level without stimulating insulin secretion (Gomez L. et al. Br. J. Nutr. 2012 June; 107(12):1739-46). As such D-fagomine has been proposed as a useful dietary ingredient or functional food component to reduce the health risks associated with an excessive intake of fast-digestible carbohydrates.

WO2011117362 discloses the capacity of D-fagomine of inhibiting bacterial adherence to mucosal surface. Since bacterial adherence to mucosa is an important prerequisite for colonization and infection, D-fagomine is considered a valuable agent for the prevention and/or coadjuvant treatment of bacterial infection. In addition, this document discloses that D-fagomine is also useful for preventing micloflora imbalance caused by enteric, oral or respiratory pathogenic bacteria. This effect is due to the fact D-fagomine adheres to harmful bacteria such as certain strains of the genus *Escherichia*, *Salmonella* or *Streptococcus* but not to healthy ones such as *Lactobacili* or *Bifidobacteria*. In these sense, healthy bacteria are more tendent to implantation in the mucosa than pathogen ones.

The research done (Gomez L, et al), also confirms that D-fagomine do not show antimicrobial activity, that means that, although there is an specific effect on the adhesion of some bacteria the viability of these bacteria are not affected by the presence of D-fagomine. Other prior art document also refer to the biological function of D-fagomine and its N-alkylated derivatives (Castillo J. A. et al. "Fructose-6-phosphate alolase in organic synthesis: preparation of D-fagomine; N-alkylated derivatives, and preliminary biological assays" Organic letter 2006 Vol. 8 (26): 6067-6070). Castillo J. A et al describes that D-fagomine and N-alkylated derivatives $C_4$, $C_6$, $C_8$, $C_9$ and $Ph-CH_2$ do not show antimicrobial activity.

Now, the authors of the present invention have discovered a new biological function of D-fagomine. In particular, they have found that D-fagomine has the capacity to trigger mechanisms of innate immune response at the level of the mucosa. The improvement of the mechanisms of innate immune response helps individuals to prevent and reduce infections from potential pathogens microorganisms near the mucosa. Additionally, this improvement of the natural mechanisms of the innate immune system protection at the mucosa level avoids the undesirable overactivation of the humoral immune response which is the second relevant defense against microorganisms. Said humoral immune response which is carried out by the adaptative immune system is generally more potent and systemic. Its overactivation contributes to the onset of chronical subclinical inflammation situations.

The improvement of innate immune response is relevant to maintain under control not only bacteria but also to virus and other parasites.

Microorganisms are considered to maintain the correct activity level in our innate immune system. It has been proposed that an unnatural development of the immune system and particularly of the innate immune system results in an increased susceptibility to autoimmune diseases. Celiac, Crohn's disease and ulcerative colitis for example, have been related to this abnormal response. The absence or malfunction of innate immune response contributes to the overactivation the humoral immune response that may result in uncontrolled damaging autoimmune responses. Up to 100 types of autoimmune disease including asthma, multiple sclerosis, lupus, psoriatic and reumathoid arthritis, and diabetes have been identified.

Also chronic subclinical inflammation derived for an altered interaction between the gut microbiota and the host is considered to potentiate the humoral inflammatory response, and is deemed to be the cause governing the rate of progression of the metabolic syndrome and other diseases such as obesity, hypertension, type II diabetes, fatty liver, Alzheimer or cancer (e.g. breast, colon).

It is then of great interest to find new ways of naturally reinforcing the innate immune response at the local mucosal level by, at the same time, decreasing the risk of undesirable potent humoral immune response.

The innate immune system represents the first line of defense of the organism and comprises the cells and mechanisms that defend the host from infection by other organisms in a non-specific manner. This means that the cells of the innate system recognize and respond to pathogens in a generic way, but unlike the adaptive immune system, it does not confer long-lasting or protective immunity to the host. Innate immune systems provide immediate defense against infection. It is formed by different types of cells such as Mast cells, phagocytes (macrophages, neutrophils and dendritic cells), basophils and eosinophils and Natural Killer cells (NK cells) as well as by biochemical mechanism such as the complement system.

The major functions of the vertebrate innate immune system include:
a) Recruiting immune cells to sites of infection, through the production of chemical factors, including specialized chemical mediators, called cytokines.
b) Activation of the complement cascade to identify bacteria, activate cells and to promote clearance of dead cells or antibody complexes.
c) The identification and removal of foreign substances present in organs, tissues, the blood and lymph, by specialised white blood cells.
d) Activation of the adaptive immune system through a process known as antigen presentation.
e) Acting as a physical and chemical barrier to infectious agents.

The present inventions is based in the demonstration made by inventors that the cells of the innate immune system present in the mucosa release cytokines such as TNF-α in the presence of D-fagomine.

The enhancement of the innate immune response in the mucosa represents a natural mechanism of protection against pathogens since it maintains a natural defense that avoids triggering the more potent, aggressive and systemic response of the adaptive immune system against pathogens capable of avoiding or hiding the natural defenses of the mucosa. The presence of an "activated" innate immune system avoids the triggering of mechanisms of acute response against certain pathogen bacteria so adapted to the medium that with the pass of time are responsible of chronical subclinical inflammatory processes.

DETAILED DESCRIPTION OF THE INVENTION

Figure 1:
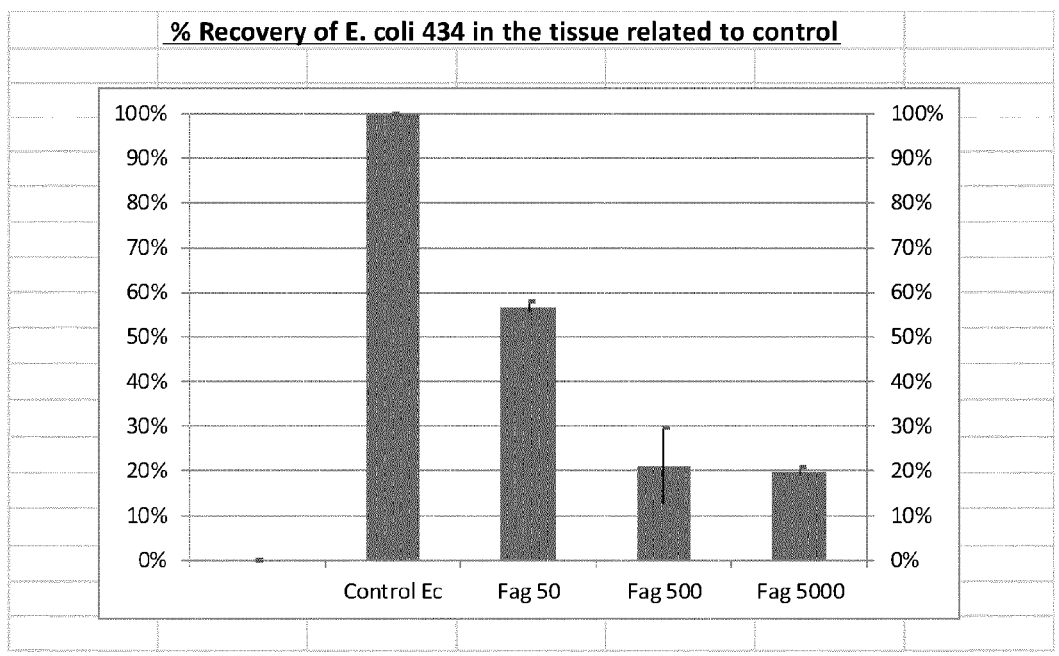
FIG. 1: represents the recovery of *E. coli* 434 from the colon mucosa. A negative control without addition of *E. coli* to the preparation was used. As positive control a sample with *E. coli* but without D-fagomine was used. In addition, three different samples of *E. coli* with D-fagomine at different doses (50, 500 and 5000 µg/ml) were tested. The results demonstrate that D-fagomine has antiadherent properties against *E. coli* in a dose dependent manner.

A first aspect of the invention refers to the compound D-fagomine or a pharmaceutical acceptable salt thereof, or a veterinary salt thereof or an edible salt thereof, for use as immunostimulating agent of innate immune system at a mucosal level and as an agent for the prevention of inflammatory processes related with an overeactivation of the humoral immune response.

The immunostimulation of the innate immune system at the mucosal level has the advantage that it decreases the incidence of more potent and potentially damaging humoral immune responses. As such the D-fagomine helps to prevent the onset of autoimmune diseases such as diabetes, psoriasis metabolic syndrome Crohn's disease, celiac disease, polymyalgia or rheumatoid arthritis, and reduces the progression of diseases related to an abnormal humoral inflammatory response, as is metabolic syndrome and other diseases such as obesity, hypertension, type II diabetes, fatty liver, Alzheimer or cancer (e.g. breast, colon).

Non-limiting D-fagomine salts which may be used within the context of the present invention are tartrate, hemitartrate, citrate, hemicitrate, chlorhidrate, malate, or acetate salts.

D-fagomine has been demonstrated to produce an immunostimulating response of the innate immune system at the level of mucosa which is the first barrier that the pathogens face in the infective process. D-fagomine activates the response of the innate immune system at the level of all types of mucosa, namely the oral mucosa, the esophageal mucosa, the gastric mucosa, enteric mucosa, the colonic mucosa, the nasal mucosa, the bronchial mucosa, the urethral mucosa or the uterine mucosa.

In a particularly preferred embodiment the activating response of the innate immune system takes place in the nasal mucosa. The activation of innate immune response in the nasal mucosa is helpful as coadyuvant for improving nasal vaccine efficacy against bacterium as *Streptococcus pneumonia* or virus as influenza. In another particularly preferred embodiment, the activating response of the innate immune system takes place in enteric mucosa. The activation of innate immune response in the enteric mucosa is helpful as coadyuvant for improving oral vaccine efficacy against some microorganisms such as vibrio strains, tuberculosis or poliovirus.

In the most preferred embodiment, the activating response of the innate immune system takes place at the level of the colon mucosa. The use of D-fagomine is especially interesting to trigger the innate immune response locally at the level of the colon for different reasons. A first one is that the colon is one of the regions with a more abundant concentration and presence of bacteria and also one of the regions with the presence of more opportunistic pathogens, including *E coli* that is ubiquitous in humans. In this sense, also the colon is one of the regions more sensible and with more likelihood of infection, hence it is important that the innate immune system is activated and under surveillance at this level of the gastrointestinal tract. The second reason is that while other kind of carbohydrates may have a similar kind of immunostimulating activity of the innate immune system, they normally do not reach the colon as they are consumed or degraded by the enteric bacteria during their transit through the gastrointestinal tract. On the contrary, D-fagomine is an iminosugar that cannot be metabolized by the enteric bacteria and as such it is capable of reaching the colon where it can exert its immunostimulating function at a local level, even at very low concentrations.

In fact, although the presence of D-fagomine in concentrations of 5000 µg/ml or less is sufficient to produce an immunostimulating effect of the innate immune system in the mucosa, it has been surprisingly observed that the lower is the concentration of D-fagomine the more potent is innate immune response. In fact, in a preferred embodiment D-fagomine is used in concentrations of 500 µg/ml or less. In a still more preferred embodiment D-fagomine is used in concentrations of 50 µg/ml or less. At concentrations of 50 µg/ml or less the production of the cytokine TNF-α is surprisingly increased. The production of TNF-α is a direct indication of the activation of the innate immune system, that is of the immunostimulation thereof.

As an agent capable of maintaining the innate immune system under "alert", the regular consumption of D-fagomine contributes to the prophylaxis and prevention of inflammatory processes related with opportunistic pathogens. In particular, it can be very useful for preventing situations of chronic or subchronic inflammation caused by bacteria capable of escaping from the immune system by the formation of biofilms that can hide the colonies from the immune system. This kind of situation tends to facilitate infection and triggers immune responses not only at a mucosal level but also at a serosal level. The existence of this type of serosal responses is the source of the chronic inflammatory state.

In a particular and preferred embodiment of the invention D-fagomine contributes to the prevention of inflammatory processes related with bacteria selected from gamma proteobacteria such as *E. coli, Salmonella tiphymurium, Pseudomonas aeruginosa* or Streptoccocci such as *S. mutans, S. mitis, S. oralis, S. pneumonia, S. pyogenes, S. agalactiae* or *Enteroccoccus faecalis*.

In the preferred embodiment of the invention D-fagomine is useful for the prevention of inflammatory processes related to overactivation of the humoral response by certain pathogenic strains of *Escherichia Coli* which have very much tendency to escape to the immune system by forming biofilms or by other strategies and to produce chronic clinical and subclinical inflammation processes.

Another aspect of the invention relates to a composition comprising D-fagomine or a pharmaceutical acceptable salt thereof, or a veterinary salt thereof or an edible salt thereof, and at least one additive for use as immunostimulating agent of innate immune system at a mucosal level and as an agent for the prevention of inflammatory processes associated to opportunistic pathogens.

Non-limiting D-fagomine salts which may be used in the composition of the invention are tartrate, hemitartrate, citrate, hemicitrate, chlorhidrate, malate, or acetate salts.

The composition of the invention may be in solid form or in the form of a liquid composition, preferably an aqueous composition.

In the case of liquid or preferably aqueous composition D-fagomine is in a concentration of 5000 µg/ml or less, preferably of 500 µg/ml or less, and more preferably of 50 µg/ml or less.

D-fagomine in the composition of the invention can be synthetic or it can be of natural origin, in the form of enriched extract from a natural source. In the case of an enriched extract from natural sources D-fagomine is preferably extracted or food produced from the seeds of *Fagopyrum esculentum* or *Fagopyrum tataricum*, leaves of *Morus bombycis* or *Morus alba*, roots of *Lycium chinense*, roots and leaves of *Xanthoceris zambesiaca*, fruits of *Angylocalyx pinaertii*, leaves of *Baphia nitida*, seeds of *Castanospermum austral* or roots of *Lonchocarpus latifolius*.

In a particularly preferred embodiment the composition of the invention comprises D-fagomine of an extract from seeds of *Fagopyrum esculentum*.

The composition of the invention can be formulated either as a pharmaceutical, veterinary or food composition, the latter being the preferred type of composition.

In a preferred embodiment the pharmaceutical composition is a mouthwash, a gel, a liquid dental cleaning lotion, a tooth paste, a chewing gum, a denture cleaner or a prothesis adherence cream. In a more preferred embodiment, the pharmaceutical composition is a chewing gum.

Furthermore, it is possible to use D-fagomine as part of a nutritional composition food, pet food and feedstuff. The food composition of the invention can also be presented as a food or a beverage additive to produce a functional food or a functional beverage. In this form it can be added to liquid food products or concentrates or powders, such as milk and liquid milk like products, various beverage including juices, soft drinks, sport drinks, alcoholic beverages, and the like. It is especially useful to have a composition of D-fagomine according to the invention as part of a food for an infant, preferably as a part of a infant formula. Also, when the D-fagomine composition comes from a buckwheat (*Fagopyrum esculentum*) purified extract it can be part of a beer, non-alcohol beer, tea like drink, milk like drink, yogurt, pasta, biscuits, cookies, cereal bars, swollen grains, bread, crepes, cakes, creams, desserts, breakfast cereals and others. The food composition or food additive of the invention can also be produced in a natural way, e.g. by having a domestic animal such a cow or other animal that produce D-fagomine in its milk. This can be accomplished by feeding the animal with *Fagopyrum esculentum, Fagopyrum tataricum, Morus alba* or purified D-fagomine.

In another embodiment, the composition of the invention also comprises rutin or other flavonol polyphenols in its formulation (i.e. hesperidin). Rutin, is the glycoside between the flavonol quercetin and the disaccharide rutinose (α-L-rhamnopyranosyl-(1→6))-β-D-glucopyranose) and has the following formula.

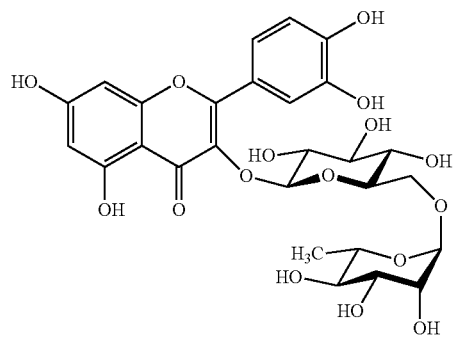

When rutin is administered orally it tends to be stable in the upper intestine, but rapidly deglycosylated to liberate the quercetin at the level of the colon (Kim H. et al. "Metabolic and pharmacological Properties of rutin, a dietary quercetin glycoside for treatment of inflammatory bowel disease" Pharmaceutical research, 2005, Vol. 22 N° 9). Quercetin has been taught to have anti-inflammatory effect, especially in the treatment of chronic inflammatory states such as inflammatory bowel disease and as such the use of rutine in the composition of the invention as a source of quercetin provides a synergistic effect in the treatment and prevention of inflammation especially at the level of the colon where on the one hand quercetin is liberated and on the other hand D-fagomine is able to arrive an exert its immunostimulating effect. The presence of rutin helps somehow to maintain under control the immune response triggered by D-fagomine.

It is moreover noted that rutin is, as D-fagomine, present in buckwheat (*Fagopyrum esculentum*) and also *Fagopyrum tataricum* that usually presents higher amounts of rutin that the *F. esculentum*. In this sense, in the preferred embodiment of the invention, the composition of the invention is elaborated from an extract of *Fagopyrum esculentum* enriched in D-fagomine and rutin.

Additional objects, advantages and features of the invention will become apparent to those skilled in the art upon examination of the description or may be learned by practice of the invention. The following examples are provided by way of illustration, and they are not intended to be limiting of the present invention. Furthermore, the present invention covers all possible combinations of particular and preferred embodiments described herein.

EXAMPLES

Example 1: Biological Activity of D-Fagomine in Human Colon Sample

The aim of this investigation was to determine the effects "ex vivo" of D-fagomine on the adhesion of *E. coli* to human colon mucosal samples and their possible influence on the release of inflammatory mediators on a range of doses as an indication of the activation of the innate immune response.

The approach, included the incubation of an *E. coli* strain with mucosal colonic samples obtained by surgery. The intention was to preserve the whole structure of mucosal samples including multiple cell populations such as epithelial cells and immunocompetent cells (macrophages, dendritic cells, plasma cells and lymphocytes), all of them keeping their original structure and disposition for cell to cell interaction. In other words, the approach was intended for mimicking the "in vivo" conditions of the colon mucosa.

In the design of the study doses of 0, 50, 500 and 5000 µg/ml of D-fagomine were tested.

Pathogenic strains of *E coli* were used. The main differences of pathogenic strains of *E coli* vs. other non pathogenic are related to their capacity to avoid the immune system.

Materials and Methods
Organ Culture:
Samples of macroscopically normal colonic mucosa were obtained at surgery from patients undergoing colectomy for colonic cancer. Areas free of disease were collected in ice-cold saline and transferred immediately to the Laboratory of the Digestive Research Unit of Hospital's Vail d'Hebron (Barcelona). After washing with saline, the mucosa was dissected from the muscularis layer and pieces between 25 and 30 mg were placed surface up in culture wells (15 mm diameter wells with 500 µm bottom mesh, Netwell culture systems, Costar, Cambridge, Mass.), and orientated so that the epithelial surface was upper-most. Filters were suspended over wells containing 1.5 ml of RPMI edium (CanSera, Rexdale, Ontario, Canada) supplemented with 10% foetal calf serum (FCS; Gibco-BRL, Eggenstein, Germany), glutamine 2 mM and antibiotics: 100 U/ml penicillin, 100 microg/ml streptomycin and 50 microg/ml gentamycin, (all from Normon, Madrid, Spain). This volume is just for maintaining the humidity of the surface but not for sinking beneath the surface.

Biopsies were incubated at 37° C. in a 95% $O_2$+5% $CO_2$ atmosphere and stimulated during 1 h with PMA (phorbol-12-myristate-13-acetate) and Ionomycin (100/1000 ng/mL), both available from Sigma.

Thereafter, medium was replaced by fresh RPMI 1640 medium (without glucose) supplemented with 10% FCS and sodium bicarbonate at 24 mmol/L.

Bacteria strain *E. coli* (10-8 CFU/ml) and fagomine (50, 500 and 5000 µg/mL) were added carefully to the explants. After 4 h of culture of tissues with *E. coli*, supernatants were collected for measurement of *E. coli* recovery, release of TNF-α, LDH (viability) and pH. Moreover, the tissues were rinsed, homogenized and assayed for *E. coli* recovery and LDH (to study tissue viability).

Bacteria Strains:
The pathogenic *E. coli* reference strain (CECT 434, (Migula 1895) Castellani and Chalmers 1919) was provided by Dr. Maria Angeles Calvo (Microbiology Laboratory, Faculty of Veterinary, Autonomous University of Barcelona, Spain)

Inoculum of *E. coli*:
The day before of the experiment with tissue, the *E. coli* strain was inoculated in Luria Bertani broth (Pharmacy, Hospital Vail d'Hebron, Autonomous University of Barcelona, Spain) at 37° C. under aerobic conditions for 24 h. The day of the experiment bacteria were harvested in the stationary phase, cell counts in the bacterial suspension were estimated by optical density at 600 nm absorbance, and bacteria were added to the tissue-culture wells at the appropriate dilution.

Rinse of Tissue:
In order to quantify only the adherent *E. coli* bacteria, at the end of the culture, tissues were recovered and rinsed with 2 ml of saline in an orbital mixer at low speed during 2 minutes. After rinsing, each tissue was homogenized in 1 ml of saline and dilutions were prepared to quantify the recovery of *E. coli* in solid agar selective media.

Recovery of *E. coli* at the End of the Experiment:
Supernatant and tissue recovery of *E. coli* was quantified immediately after the experiment by culturing in selective solid media for Enterobacteriaceae. At least 3 different dilutions were carried out for each sample. The number of colonies was manually counted 24 hours later. The results have been normalized to a standard size of 30 mg.

TNF-α Quantification:
Concentration of TNF-α in the supernatants was measured using a commercially available ELISA assay system for human citoquine TNF-α (Ready to Set, e-Bioscience). Cytokine concentration is expressed as pg (TNF-α) per 30 mg of tissue.

Colon Viability:
To estimate tissue viability, we calculated LDH (lactate-dehydrogenase) activity release in the supernatant. This method was validated by Finnie (Gut 1995). The ratio of LDH activity in the supernatant over total LDH activity in tissue homogenates was calculated and used to estimate the percentage of viable tissue. Tissue samples were homogenized in Tris/HCl (100 mmol/L, pH 7.4) and supernatants were analysed for LDH using the spectrophotometric method. Tissue viability was assessed as the release of LDH per mg of tissue.

Statistical Analysis:

Results are expressed by the mean and sem, or by individual data in plots.

Results

Recovery of E. coli in Tissue at the End of the Experiment:

The result in the recovery of E. coli in tissue samples are provided in table 1 and FIG. 1:

TABLE 1

|  |  | Control Ec | Fag 50 | Fag 500 | Fag 5000 |
|---|---|---|---|---|---|
| E coli × 10 6 | 1 | 8.2 | 4 | 2.4 | 1.6 |
| Recovery on tissue | 2 |  | 4.4 | 0.8 | 1.6 |
| E coli × 10 6 | 1 | 7.45 | 4.12 | 2.21 | 1.4 |
| Standarized 30 mg | 2 |  | 4.31 | 0.9 | 1.55 |
| Average |  | 7.45 | 4.22 | 1.56 | 1.47 |
| SEM |  |  | 0.09 | 0.65 | 0.07 |
| Average % over control |  | 100.0% | 56.6% | 21.0% | 19.8% |
| SEM % over control |  |  | 1.3% | 8.7% | 1.0% |

As can be clearly observed the higher presence of E. coli in colon tissue is shown in the control sample and the presence of bacteria adhered to the tissue decreases as the concentration of D-fagomine increases. In other words it can be inferred that D-fagomine has an antiadherent effect against E. coli on the colon epithelium. The antiadherent effect is more potent while the concentration of D-fagomine increases.

Figure 2:
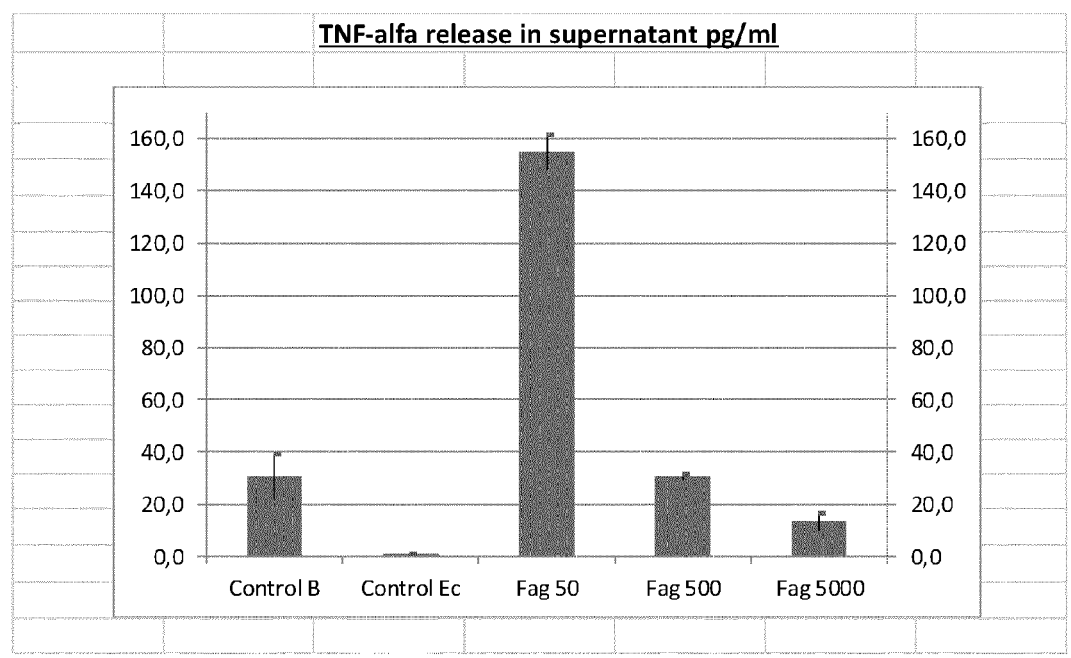
FIG. 2: represents the TNF-alfa release by the cells from the innate immune system present in the colon mucosa. The TNF was measured from the supernatant. As in FIG. 1 negative control without addition of *E. coli* to the preparation and positive control with *E. coli* but without D-fagomine was used. Again three different samples of *E. coli* with D-fagomine at different doses (50, 500 and 5000 µg/ml) were tested. The results demonstrate that D-fagomine has the capacity to stimulate the release of TNF-alfa and that the lower is the dose the more potent is such release. This is a direct indication that D-fagomine has an immunostimulating effect on the innate immune system helping the immune system detecting and attacking microorganisms at the mucosa level.

Cytokine Release:

The results of cytokine release are shown in table 2 and FIG. 2:

TABLE 2

|  |  | Control B | Control Ec | Fag 50 | Fag 500 | Fag 5000 |
|---|---|---|---|---|---|---|
| TNF-alfa/ml | 1 | 12.9 | 0.7 | 106.2 | 20.7 | 13.8 |
|  | 2 | 25.2 | 0.4 | 98.8 | 18.6 | 5.7 |
| mg (tissue weight) | 1 | 31.2 | 33.0 | 29.1 | 32.6 | 34.3 |
|  | 2 | 26.5 | 33.6 | 30.6 | 26.2 | 31.0 |
| TNF-alfa (1.5 ml standarized 30 mg | 1 | 18.6 | 0.9 | 164.2 | 28.6 | 18.1 |
|  | 2 | 42.8 | 0.5 | 145.4 | 31.9 | 8.2 |
| Average |  | 30.7 | 0.7 | 154.8 | 30.3 | 13.2 |
| SEM |  | 8.5 | 0.1 | 6.7 | 1.2 | 3.5 |

The results clearly demonstrate that the presence of D-fagomine has the effect of stimulating the release of TNF-alfa either with respect to the control with E. coli or with respect to the control without E. coli. In addition, it is noticeable that the release of TNF-alfa is dependent on D-fagomine concentration. It is interesting to see that the lowest is the concentration of D-fagomine the more potent is the cytokine release. TNF-alfa release at the dosage of 50 µg/mL is surprisingly potent as it induces a TNF-alfa release which is 5 times higher to that of the dose of 500 µg/mL and nearly 8 times higher to that of the dose of 5000 µg/mL.

In brief this assay demonstrates that D-fagomine induces the activation of the innate immune response in a dose dependent form and that said induction is more potent at lower concentrations of 50 µg/mL or less.

Control on Viability:

The results of c viability of colon tissue are represented in table 3:

TABLE 3

|  | Viability LDH | pH |
|---|---|---|
| Blank | 93.25% | 7.71 |
| Ec | 94.16% | 7.62 |
| Ec Fago 50 | 88.20% | 7.65 |
| Ec Fago 500 | 91.47% | 7.59 |
| Ec Fago 5000 | 83.88% | 7.65 |

The results indicate that the coculture with E. coli or fagomine does not affect the viability of the tissue.

Example 2: Compositions Comparing D-Fagomine

The following compositions with D-fagomine were prepared:

Drink beverage supplemented with D-fagomine (50 mg) and rutin (500 mg).

Tablet supplemented with D-fagomine (50 mg) and rutin (500 mg).

Biscuits made of Fagopyrum esculentum flour which naturally comprises D-fagomine, rutin and a preparation of prebiotics containing plant fibers, FOS (Fructooligosacharides) and XOS (Xylooligoscharides)

Alcohol free beer made from Fagopyrum esculentum with a content of 8 ppm of D-fagomine and 50 ppm rutin.

Infant formula, based on milk from cows feeded with buckwheat showing a content of D-fagomine 10 ppm.

Sugar free chewing gum with D-fagomine (50 mg) for stimulating the innate immune response in the oral mucosa and preventing caries and periodontal diseases.

Candy with D-fagomine (20 mg) as coajyuvant in processes of bacterial infection in the throat or in guts.

Pellet, micro-encapsulation preparation with D-fagomine (50 mg) and rutin (500 mg) as additive for the preparation of functional foods or pharmaceutical formulations, to improve bioavailability in the colon.

Nasal spray with D-fagomine (10 mg) as coadjuvant for nasal vaccines in processes of immunization against Streptococcus pneumoniae, influenza virus etc.

Oral powder formulation of 50-100 mg D-fagomine as coadjuvant in processes of enteric infections, together with probiotics (lactobacillus, bifidobacteria).

The invention claimed is:

1. A method of immunostimulating the innate immune system in a subject suffering from the onset of an autoimmune disease selected from the group consisting of Crohn's disease, ulcerative colitis, celiac disease, psoriasis, polymyalgia, and rheumatoid arthritis, the method comprising administering D-fagomine to the subject in an amount effective to stimulate the innate immune system of the subject's mucosa.

2. The method of claim 1 wherein the innate immune system is at the level of the oral mucosa, the esophageal mucosa, the gastric mucosa, enteric mucosa, the colonic mucosa, the nasal mucosa, the bronchial mucosa, the urethral mucosa or the uterine mucosa.

3. The method of claim 1 wherein the innate immune system is at the level of the colonic mucosa.

4. The method of claim 1 wherein the D-fagomine is administered in the form of a solid or aqueous composition.

5. The method of claim 1 wherein the D-fagomine is administered in the form of an aqueous composition and the amount of D-fagomine in the aqueous composition is less than 500 µg/ml.

6. The method of claim 5 wherein the amount of D-fagomine in the aqueous composition is between 50 and 500 µg/ml.

7. The method of claim 1 wherein the D-fagomine is administered in the form of an enriched extract from a natural source or a fine chemical.

8. The method of claim 7 wherein the natural source of D-fagomine is the seeds of *Fagopyrum esculentum* or *Fagopyrum tataricum*, leaves of *Morus bombycis* or *Morus alba*, roots of *Lycium chinense*, roots and leaves of *Xanthoceris zambesiaca*, fruits of *Angylocalyx pinaertii*, leaves of *Baphia nitida*, seeds of *Castanospermum austral* or roots of *Lonchocarpus latifolius*.

9. The method of claim 1 wherein the D-fagomine is administered in the form of a pharmaceutical, veterinary or food composition.

10. The method of claim 1 wherein the D-fagomine is administered in combination with at least one additive.

11. The method of claim 1 wherein the D-fagomine is administered in combination with rutin.

12. The method of claim 1 wherein the administering increases production of TNF-$\alpha$.

13. The method of claim 1 wherein the autoimmune disease is Crohn's disease.

14. The method of claim 1 wherein the autoimmune disease is ulcerative colitis.

15. The method of claim 1 wherein the autoimmune disease is celiac disease.

16. The method of claim 1 wherein the autoimmune disease is psoriasis.

17. The method of claim 1 wherein the autoimmune disease is polymyalgia.

18. The method of claim 1 wherein the autoimmune disease is rheumatoid arthritis.

\* \* \* \* \*